United States Patent
Wu et al.

(10) Patent No.: US 12,187,667 B2
(45) Date of Patent: *Jan. 7, 2025

(54) PREPARATION SYSTEMS AND PREPARATION METHODS FOR HIGH-QUALITY XYLITOL CRYSTALS

(71) Applicant: ZHEJIANG HUAKANG PHARMACEUTICAL CO., LTD., Zhejiang (CN)

(72) Inventors: Qiang Wu, Quzhou (CN); Mian Li, Quzhou (CN); Wenyao Zhang, Quzhou (CN); Wulong Yang, Quzhou (CN); Weidong Xu, Quzhou (CN); Shufang Qin, Quzhou (CN); Ni Zhen, Quzhou (CN)

(73) Assignee: ZHEJIANG HUAKANG PHARMACEUTICAL CO., LTD., Quzhou (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/657,754

(22) Filed: May 7, 2024

(65) Prior Publication Data

US 2024/0286984 A1 Aug. 29, 2024

Related U.S. Application Data

(63) Continuation-in-part of application No. PCT/CN2023/096366, filed on May 25, 2023.

(30) Foreign Application Priority Data

Dec. 9, 2022 (CN) .......................... 202211583786.5

(51) Int. Cl.
C07C 29/78 (2006.01)
A23L 27/30 (2016.01)
(Continued)

(52) U.S. Cl.
CPC ............ *C07C 29/78* (2013.01); *B01D 9/0059* (2013.01); *B01D 9/0063* (2013.01);
(Continued)

(58) Field of Classification Search
CPC ....... C07C 29/78; C07C 29/76; B01D 9/0059; B01D 9/0063; B01D 15/361; B01D 21/262; B01D 36/045; B01D 2009/0086
See application file for complete search history.

(56) References Cited

U.S. PATENT DOCUMENTS 4,066,711 A    1/1978   Melaja et al.

FOREIGN PATENT DOCUMENTS

CN    109438184 A    3/2019
CN    110894180 A    3/2020
(Continued)

OTHER PUBLICATIONS

International Search Report in PCT/CN2023/096366 mailed on Aug. 22, 2023, 10 pages.
(Continued)

*Primary Examiner* — Jafar F Parsa
(74) *Attorney, Agent, or Firm* — METIS IP LLC

(57) ABSTRACT

Disclosed is a preparation system and a preparation method for high-quality xylitol crystals. The preparation system comprises a blending tank, a heat exchanger, a decolorization tank, an ion exchange system, a microporous filter, a first evaporator, a first crystallization kettle, a first centrifuge, a fluidization drying bed, a xylitol dissolution tank, a second evaporator, a second crystallization kettle, a second centrifuge, a hot air drying tank, and a cold air fluidization bed sequentially connected through pipelines. Liquid outlet of the first centrifuge is connected with first inlet of the blending tank. Liquid outlet of the second centrifuge is connected with first inlet of the xylitol dissolution tank. The
(Continued)

blending tank is provided with second inlet for receiving xylitol hydrogenation solution. The xylitol dissolution tank is provided with water inlet for pure water. The material output from a product outlet of the cold air fluidization bed is xylitol crystal product. First prepared xylitol crystals are redissolved and recrystallized to prepare xylitol crystals with higher pH and better flavor.

11 Claims, 6 Drawing Sheets

(51) Int. Cl.
  *B01D 9/00* (2006.01)
  *B01D 15/36* (2006.01)
  *B01D 21/26* (2006.01)
  *B01D 36/04* (2006.01)
  *B01D 61/18* (2006.01)
  *C07C 29/76* (2006.01)

(52) U.S. Cl.
  CPC ......... *B01D 15/361* (2013.01); *B01D 21/262* (2013.01); *B01D 36/045* (2013.01); *B01D 61/18* (2013.01); *C07C 29/76* (2013.01); *A23L 27/34* (2016.08); *B01D 2009/0086* (2013.01)

(56) References Cited

FOREIGN PATENT DOCUMENTS

| CN | 111777493 A | 10/2020 |
|---|---|---|
| CN | 112442556 A | 3/2021 |
| CN | 112661796 A | 4/2021 |
| CN | 115888165 A | 4/2023 |
| CN | 218910201 U | 4/2023 |

OTHER PUBLICATIONS

Written Opinion in PCT/CN2023/096366 mailed on Aug. 22, 2023, 11 pages.

PREPARATION SYSTEMS AND PREPARATION METHODS FOR HIGH-QUALITY XYLITOL CRYSTALS

CROSS-REFERENCE TO RELATED APPLICATIONS

This application is a continuation-in-part application of International Application No. PCT/CN2023/096366, filed on May 25, 2023, which claims priority to Chinese Patent Application No. 202211583786.5, filed on Dec. 9, 2022, the contents of each of which are incorporated herein by reference.

TECHNICAL FIELD

The present disclosure relates to the technical field of xylitol preparation, and in particular to a preparation system and a preparation method for high-quality xylitol crystals.

BACKGROUND

At present, the industrial production of xylitol is primarily based on chemical hydrogenation method, specifically, agricultural fiber waste containing hemicellulose is hydrolyzed with dilute acid, then the hydrolysate is neutralized, decolorized, concentrated, and crystallized to obtain xylose crystals, the xylose crystals are then dissolved into a specific concentration of xylose solution, which is reduced to xylitol by hydrogenation, and finally xylitol crystals are obtained by performing ion exchange, vacuum concentration, cooling crystallization, centrifugation, drying, and other steps. In order to improve the yield of xylitol products, centrifugal mother liquor is often blended with hydrogenation solution, resulting in the presence of 4-6% heterosaccharides and sugar alcohols in the blending solution. These heterosaccharides and sugar alcohols has low influence on crystallization process of xylitol, but can reduce the pH of xylitol product, which ultimately leads to a great difference in flavor of xylitol product.

In the production process of xylitol, there are two main factors can affect the pH of the product, one of which is ion exchange process. When xylitol solution passes through cation and anion exchange columns, $H^+$ and $OH^-$ in resins are exchanged out, respectively. Due to the difference of exchange capacity between cation exchange column and anion exchange column, xylitol crystal products may have different pH. The other factor affecting the pH of xylitol product is the difference in composition of xylitol solution, which leads to a great difference in the pH of xylitol crystal. Since acidity coefficients (pKa) of heterosaccharides such as glucose and xylose are smaller than xylitol, as shown in Table 1, when there is a certain amount of heterosaccharides in xylitol concentrate solutions, the prepared xylitol crystals have a relatively low pH value and relatively variable flavor, as shown in Table 2.

TABLE 1

Acidity coefficients of common sugar alcohols

| Category | Xylitol | Glucose | Xylose | Arabinose | galactose |
|---|---|---|---|---|---|
| Acidity coefficient (pKa) | 13.24 ± 0.2 | 12.43 | 12.14 | 12.46 ± 0.2 | 12.35 |

TABLE 2 pH of xylitol crystal prepared from xylitol solutions with different compositions

| Composition of xylitol solutions | 100% xylitol | 97% xylitol + 3% sorbitol | 97% xylitol + 3% glucose |
|---|---|---|---|
| pH of xylitol crystal | 6.02 | 5.72 | 5.76 |

At present, there are two main methods to increase the pH of xylitol crystal, one of which is adding a new exchange column of strong alkali resin or mixed bed resin after ion exchange process, as disclosed in the patent references of CN109438184A and CN110894180A; the other of which is adding a small amount of alkali to ion exchange solution, as disclosed in the patent reference of CN112661796A. Both of these methods achieve the purpose of increasing the pH of xylitol crystals by increasing the pH of xylitol concentrate solution. However, the problem that the xylitol prepared by conventional process has a relatively low pH and a great flavor difference is not essentially solved.

Therefore, it is desirable to provide a preparation system and a preparation method for high-quality xylitol crystals to increase the pH of xylitol crystals and improve the flavor of xylitol products.

SUMMARY

One or more embodiments of the present disclosure provide a preparation system for high-quality xylitol crystals. The preparation system may comprise a blending tank, a heat exchanger, a decolorization tank, an ion exchange system, a microporous filter, a first evaporator, a first crystallization kettle, a first centrifuge, a fluidization drying bed, a xylitol dissolution tank, a second evaporator, a second crystallization kettle, a second centrifuge, a hot air drying tank, and a cold air fluidization bed which are sequentially connected through pipelines. The first centrifuge and the second centrifuge may be provided with liquid outlet, respectively. The liquid outlet of the first centrifuge may be connected with first inlet of the blending tank through pipeline. The liquid outlet of the second centrifuge may be connected with first inlet of the xylitol dissolution tank through pipeline. The blending tank may be provided with second inlet for receiving material to be treated. The xylitol dissolution tank may be provided with water inlet for pure water. The cold air fluidization bed may be provided with product outlet. The material to be treated may be xylitol hydrogenation solution. The material output from product outlet of the cold air fluidization bed may be xylitol crystal product.

In some embodiments, the preparation system may further comprise a microprocessor and an image sensor. The image sensor may be arranged near a view window of a crystallization kettle and configured to obtain a solution image. The crystallization kettle may include the first crystallization kettle or the second crystallization kettle. The microprocessor may be configured to: determine, based on the solution image obtained from the image sensor, a crystallization precipitation rate of the crystallization kettle within at least one time interval; determine, based on the crystallization precipitation rate within the at least one time interval, a current crystallization phase; and determine, based on the current crystallization phase, a current crystallization precipitation rate, and a current temperature of the crystallization kettle, a target temperature regulation amount of the crystallization kettle.

In some embodiments, the microprocessor may be further configured to: determine, based on the solution image obtained from the image sensor, the crystallization precipitation rate of the crystallization kettle within the at least one time interval through a crystallization rate determination model. The crystallization rate determination model may be a machine learning model.

In some embodiments, the microprocessor may be further configured to: predict, based on a candidate regulation parameter, the current crystallization phase, the current crystallization precipitation rate, and the current temperature of the crystallization kettle, a crystallization precipitation rate increment corresponding to the candidate regulation parameter through a precipitation prediction model, the precipitation prediction model being a machine learning model; and determine, based on the crystallization precipitation rate increment, the target temperature regulation amount of the crystallization kettle.

One or more embodiments of the present disclosure provide a preparation method for high-quality xylitol crystals. The preparation method may be applied to the preparation system for the high-quality xylitol crystals. The preparation method may comprise the following steps: step 1, preparing xylitol concentrate solution, including blending and mixing xylitol hydrogenation solution with primary centrifugal mother liquor delivered from first centrifuge in a first proportion to obtain mixed material solution, and then performing a heat exchange treatment by heat exchanger, a decolorization treatment by decolorization tank, an ion exchange treatment by ion exchange system, a filtration treatment by microporous filter, and an evaporation treatment by first evaporator on the mixed material solution, respectively, to obtain xylitol concentrate solution; wherein a concentration of the xylitol concentrate solution may be within a range of 1200-1400 g/L, and a purity of the xylitol concentrate solution may be within a range of 94-96%; step 2, crystallizing the xylitol concentrate solution, including cooling and crystallizing the xylitol concentrate solution in first crystallization kettle for 8-12 h to obtain xylitol sugar paste, performing a separation treatment by first centrifuge and a drying treatment by fluidization drying bed on the xylitol sugar paste to obtain crude xylitol crystal, and the primary centrifugal mother liquor obtained by separation treatment of the first centrifuge back-setting to blending tank through pipeline to be blended with xylitol hydrogenation solution for reuse; wherein the purity of the crude xylitol crystal may be within a range of 98.5-99.8%, and pH<5.0, and the purity of the primary centrifugal mother liquor may be within a range of 88-92%; and step 3, dissolving and recrystallizing of crude xylitol crystal, including delivering the crude xylitol crystal to xylitol dissolution tank to be dissolved by adding pure water, and then blending and mixing dissolved crude xylitol crystal with secondary centrifugal mother liquor delivered from second centrifuge in a second proportion to obtain dissolved xylitol mixture, the dissolved xylitol mixture then concentrated by second evaporator, crystallized by second crystallization kettle, centrifuged by second centrifuge, dried by hot air of hot air drying tank, and dried by cold air of cold air fluidization bed in turn to obtain xylitol crystal product, and the second centrifugal mother liquor obtained by separation treatment of the second centrifuge back-setting to xylitol dissolution tank through pipeline to be mixed with crude xylitol crystal solution for reuse; wherein the purity of the xylitol crystal product may be greater than 99.8%, and pH>6.0.

In some embodiments, in the step 1, a temperature of the xylitol concentrate solution may be within a range of 90-100° C.

In some embodiments, in the step 2, xylitol crystal seeds may be added during the cooling and crystallization process. An addition proportion of xylitol crystal seeds may be within a range of 0.001-0.002% of solution mass, a mesh number of xylitol crystal seeds may be within a range of 60-120 mesh, and a system temperature at same time of adding the xylitol crystal seeds may be within a range of 64-66° C.

In some embodiments, in the step 3, xylitol crystal seeds may be added during the crystallization process in the second crystallization kettle. An addition proportion of xylitol crystal seeds may be within a range of 0.001-0.002% of solution mass, a mesh number of the xylitol crystal seeds may be within a range of 60-120 mesh, and a system temperature at same time of adding xylitol crystal seeds may be within a range of 64-66° C.

In some embodiments, the preparation method may further comprise: determining, based on a solution image of the crystallization kettle obtained from an image sensor, a crystallization precipitation rate of the crystallization kettle within at least one time interval; determining, based on the crystallization precipitation rate within the at least one time interval, a current crystallization phase; and determining, based on the current crystallization phase, a current crystallization precipitation rate, and a current temperature of the crystallization kettle, a target temperature regulation amount of the crystallization kettle. The crystallization kettle may be a first crystallization kettle or a second crystallization kettle.

In some embodiments, the determining, based on a solution image of the crystallization kettle obtained from an image sensor, a crystallization precipitation rate of the crystallization kettle within at least one time interval may include: determining, based on the solution image obtained from the image sensor, the crystallization precipitation rate of the crystallization kettle within the at least one time interval through a crystallization rate determination model. The crystallization rate determination model may be a machine learning model.

In some embodiments, the determining a target temperature regulation amount may include: predicting, based on a candidate regulation parameter, the current crystallization phase, the current crystallization precipitation rate, and the current temperature of the crystallization kettle, a crystallization precipitation rate increment corresponding to the candidate regulation parameter through a precipitation prediction model, the precipitation prediction model being a machine learning model; and determining, based on the crystallization precipitation rate increment, the target temperature regulation amount of the crystallization kettle.

One or more embodiments of the present disclosure provide a processing device comprising at least one processor and at least one storage. The at least one storage may be configured to store computer instructions. The at least one processor may be configured to execute at least a part of the computer instructions to implement the preparation method for the high-quality xylitol crystals.

One or more embodiments of the present disclosure provide a non-transitory computer-readable storage medium comprising computer instructions that, when read by a computer, may direct the computer to implement the preparation method for the high-quality xylitol crystals.

BRIEF DESCRIPTION OF THE DRAWINGS

The present disclosure is further illustrated by way of exemplary embodiments, which is described in detail with reference to the accompanying drawings. These embodiments are not limiting. In these embodiments, the same numbering indicates the same structure, wherein.

DETAILED DESCRIPTION

Figure 1:
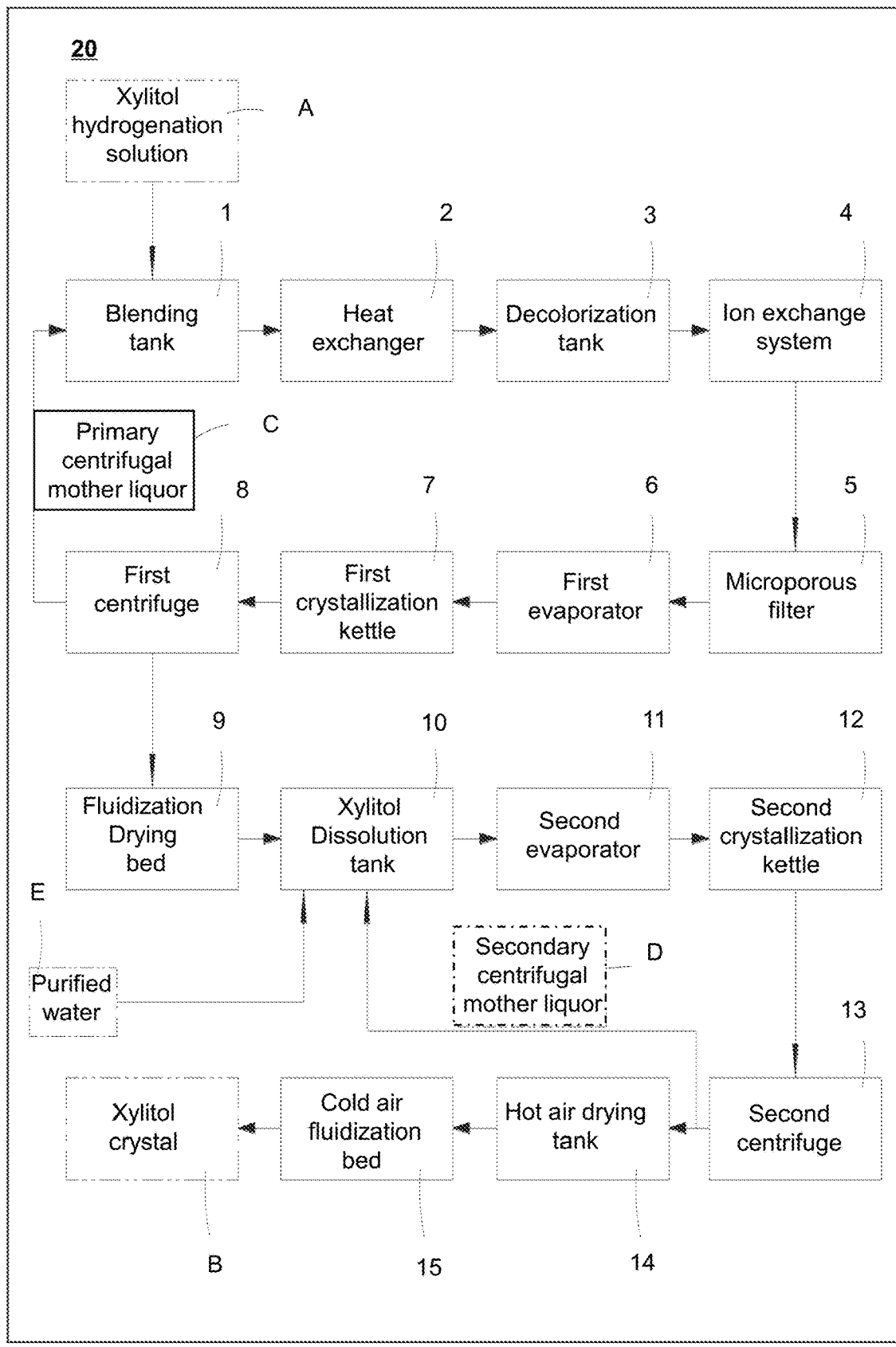
FIG. 1 is a structural block diagram illustrating a preparation system for high-quality xylitol crystals according to some embodiments of the present disclosure.

In order to illustrate the technical solutions of the embodiments of the present disclosure more clearly, the following briefly introduces the drawings that need to be used in the description of the embodiments. Apparently, the accompanying drawings in the following description are only some examples or embodiments of the present disclosure, and those skilled in the art can also apply the present disclosure to other similar scenarios according to the drawings without creative efforts. Unless obviously obtained from the context or the context illustrates otherwise, the same numeral in the drawings refers to the same structure or operation.

It should be understood that "system" and/or "device" as used herein is a method for distinguishing different components, elements, parts, portions or assemblies of different levels. However, the words may be replaced by other expressions if other words can achieve the same purpose.

As indicated in the disclosure and claims, the terms "a", "an" and/or "the" are not specific to the singular form and may include the plural form unless the context clearly indicates an exception. Generally speaking, the terms "comprising" and "including" only suggest the inclusion of clearly identified steps and elements, and these steps and elements do not constitute an exclusive list, and the method or device may also contain other steps or elements.

The flowchart is used in the present disclosure to illustrate the operations performed by the system according to the embodiments of the present disclosure. It should be understood that the preceding or following operations are not necessarily performed in the exact order. Instead, various steps may be processed in reverse order or simultaneously. Meanwhile, other operations may be added to these procedures, or a certain step or steps may be removed from these procedures.

As for how to improve pH of xylitol crystals, CN 109438184 A discloses a method for improving and stabilizing pH of crystalline xylitol, in which a group of mixed bed resin is added after an ion exchange process, and pH of dissolved crystalline xylitol is improved and stabilized by the treatment of the mixed bed resin. However, pH of xylitol crystals is improved by increasing pH of xylitol concentrate solution, and pH of prepared xylitol is not essentially improved, which still leads to a low pH of the produced xylitol.

Therefore, in some embodiments of the present disclosure, first prepared xylitol crystals may be dissolved by adding water in a certain proportion to obtain xylitol solution with high purity, and then the xylitol solution may be recrystallized to prepare xylitol crystals with high pH and better flavor, so that the pH of the xylitol crystals can be improved and the pH can be maintained stable for a long time, and the flavor of the xylitol crystals can also be effectively improved.

FIG. 1 is a structural block diagram illustrating a preparation system for high-quality xylitol crystals according to some embodiments of the present disclosure. In some embodiments, as illustrated in FIG. 1, a preparation system 20 for high-quality xylitol crystals may comprise a blending tank 1, a heat exchanger 2, a decolorization tank 3, an ion exchange system 4, a microporous filter 5, a first evaporator 6, a first crystallization kettle 7, a first centrifuge 8, a fluidization drying bed 9, a xylitol dissolution tank 10, a second evaporator 11, a second crystallization kettle 12, a second centrifuge 13, a hot air drying tank 14, and a cold air fluidization bed 15 which are sequentially connected through pipelines.

The blending tank 1 refers to a mixing device that blends and admixes a plurality of substances. In some embodiments, the blending tank 1 may be provided with first inlet. The first inlet of the blending tank 1 may be connected with liquid outlet of the first centrifuge through pipeline. The first inlet may be configured to receive primary centrifugal mother liquor from the first centrifuge. In some embodiments, the blending tank 1 may be provided with second inlet for receiving material to be treated. The material to be treated may be xylitol hydrogenation solution A. Correspondingly, in some embodiments, the blending tank 1 may blend the primary centrifugal mother liquor C with the xylitol hydrogenation solution A to obtain mixed material solution. More descriptions regarding the primary centrifugal mother liquor C, the xylitol hydrogenation solution A, and the mixed material solution may be found in FIG. 2 and related descriptions thereof.

The heat exchanger 2 refers to a device that transfers a portion of heat from hot fluid to cold fluid. In some embodiments, the heat exchanger 2 may receive the mixed material solution from the blending tank 1, and perform a heat exchange treatment on the mixed material solution, such that temperature of the mixed material solution after the heat exchange treatment may satisfy a predetermined temperature condition. For example, the heat exchanger 2 may perform the heat exchange treatment on the mixed material solution using hot fluid of predetermined temperature, such that the temperature of the mixed material solution after the heat exchange treatment may be within a range of 90-100° C. More descriptions regarding the predetermined temperature condition may be found in FIG. 2 and related descriptions thereof.

The decolorization tank 3 refers to a device for performing a decolorization treatment on fluid. The decolorization treatment may include one or more treatments such as an ultrafiltration decolorization treatment, adsorption decolorization treatment, a flocculation decolorization treatment, or the like. In some embodiments, the decolorization tank 3 may receive the mixed material solution after a heat treatment of the heat exchanger 2 to perform the decolorization treatment on the mixed material solution after the heat treatment to obtain the mixed material solution after the decolorization treatment.

The ion exchange system 4 refers to a system device in which ions in solution are exchanged with ions on an ion exchange agent. In some embodiments, the ion exchange agent may be classified as a cation exchange column and an anion exchange column. The ion exchange agent may include one or more types of ion exchange resins, ion exchange cellulose, an ion exchange gel, or the like.

In some embodiments, the ion exchange system 4 may receive the mixed material solution after the decolorization treatment from the decolorization tank 3 to perform an ion exchange treatment on the mixed material solution after the decolorization treatment to obtain the mixed material solution after the ion exchange treatment. The ion exchange treatment refers to treatment process in which when the mixed material solution after the decolorization treatment passes through ion exchange resin, $H^+$ and $OH^-$ in the ion exchange resin may be exchanged out, respectively.

The microporous filter 5 refers to a device that traps interfering particles such as particles, bacteria, contaminants, or the like from gases and liquids. In some embodiments, the microporous filter 5 may receive the mixed material solution after the ion exchange treatment from the ion exchange system 4 to perform a filtration treatment on the mixed material solution after the ion exchange treatment to obtain the mixed material solution after the filtration treatment.

An evaporator refers to a device that converts liquid in solution to gas. In some embodiments, the evaporator may achieve an evaporation treatment and a concentration treatment of liquid by evaporating the liquid in the solution.

In some embodiments, the evaporator may include the first evaporator 6. The first evaporator 6 may receive the mixed material solution after the filtration treatment from the microporous filter 5 to perform the evaporation treatment on the mixed material solution after the filtration treatment to obtain xylitol concentrate solution. More descriptions regarding the xylitol concentrate solution may be found in FIG. 2 and related descriptions thereof.

In some embodiments, the evaporator may include the second evaporator 11. The second evaporator 11 may receive dissolved xylitol mixture from the xylitol dissolution tank 10 to perform the concentration treatment on the dissolved xylitol mixture to obtain the dissolved xylitol mixture after the concentration treatment. More descriptions regarding the xylitol dissolution tank 10 may be found in the related descriptions below. More descriptions regarding the dissolved xylitol mixture may be found in FIG. 2 and related descriptions thereof.

A crystallization kettle refers to a device for crystallizing material after a mixing reaction by cooling. In some embodiments, the crystallization kettle may include the first crystallization kettle 7. The first crystallization kettle 7 may receive the xylitol concentrate solution from the first evaporator 6 to perform a cooling and crystallization treatment on the xylitol concentrate solution to obtain xylitol sugar paste. More descriptions regarding the xylitol sugar paste may be found in FIG. 2 and related descriptions thereof.

In some embodiments, the crystallization kettle may include the second crystallization kettle 12. The second crystallization kettle 12 may receive the dissolved xylitol mixture after the concentration treatment from the second evaporator 11 to perform the crystallization treatment on the dissolved xylitol mixture after the concentration treatment to obtain the dissolved xylitol mixture after the crystallization treatment.

A centrifuge refers to a mechanical device that separates mixture of liquid from solid particle, or mixture of liquids using centrifugal force. In some embodiments, the centrifuge may include the first centrifuge 8. The first centrifuge 8 may receive the xylitol sugar paste from the first crystallization kettle 7 to perform a separation treatment on the xylitol sugar paste to obtain first material to be dried and primary centrifugal mother liquor C.

In some embodiments, the first centrifuge 8 may be provided with liquid outlet. The liquid outlet of the first centrifuge 8 may be connected with the first inlet of the blending tank 1 through pipeline, so as to output the primary centrifugal mother liquor C to the blending tank 1. More descriptions regarding the first material to be dried and the first centrifugal mother liquor C may be found in FIG. 2 and related descriptions thereof.

In some embodiments, the centrifuge may include the second centrifuge 13. The second centrifuge 13 may receive the dissolved xylitol mixture after the cooling and crystallization treatment from the second crystallization kettle 12 to perform a separation treatment on the dissolved xylitol mixture to obtain second material to be dried and secondary centrifugal mother liquor D.

In some embodiments, the second centrifuge 13 may be provided with liquid outlet. The liquid outlet of the second centrifuge 13 may be connected with the first inlet of the xylitol dissolution tank 10 through pipeline, so as to output the secondary centrifugal mother liquor D to the xylitol dissolution tank 10. More descriptions regarding the second material to be dried and the second centrifugal mother liquor D may be found in FIG. 2 and related descriptions thereof.

The fluidization drying bed 9 refers to a device for heat transfer and moisture transfer between material and gas by delivering gas to cause movement of material particles on gas distribution plate. For example, the fluidization drying bed 9 may perform a drying treatment on the first material to be dried by delivering gas to the first material to be dried.

In some embodiments, the fluidization drying bed 9 may include one or more types of a vibration fluidization bed dryer, an agitation fluidization bed dryer, a centrifugal fluidization bed dryer, or the like. In some embodiments, the fluidization drying bed 9 may receive the first material to be dried from the first centrifuge 8 to perform the drying treatment on the fluidization drying bed 9 to obtain crude xylitol crystals. More descriptions regarding the first material to be dried and the crude xylitol crystals may be found in FIG. 2 and related descriptions thereof.

The xylitol dissolution tank 10 refers to a device that dissolves the crude xylitol crystals using solvent. In some embodiments, the xylitol dissolution tank 10 may be provided with first inlet. The first inlet of the xylitol dissolution tank 10 may be connected with the liquid outlet of the second centrifuge 13 to receive the secondary centrifugal mother liquor D of the second centrifuge 13. In some embodiments, the xylitol dissolution tank 10 may be provided with water inlet for receiving pure water. In some embodiments, the pure water may be added into the xylitol dissolution tank 10 to dissolve the crude xylitol crystals, and the secondary centrifugal mother liquor D may be added into the xylitol dissolution tank 10 in a second predetermined proportion for blending and mixing to obtain the dissolved xylitol mixture. More descriptions regarding the pure water, the second predetermined proportion, and the dissolved xylitol mixture may be found in FIG. 2 and related descriptions thereof.

The hot air drying tank 14 refers to a device that makes heating medium (e.g., air, inert gas, or other hot gases) directly contact with solid particles to be dried to perform a hot air drying treatment. In some embodiments, the hot air drying tank 14 may receive the second material to be dried from the second centrifuge 13 to perform the hot air drying treatment on the second material to be dried to obtain the second material to be dried after the hot air drying treatment. More descriptions regarding the second material to be dried and the second material to be dried after the hot air drying treatment may be found in FIG. 2 and related descriptions thereof.

The cold air fluidization bed 15 refers to a device for performing a cold air drying treatment by utilizing cold air to cause particles of material to be dried to move across gas distribution plate. In some embodiments, the cold air fluidization bed 15 may be provided with product outlet. A material output from the product outlet may be xylitol crystal product B. In some embodiments, the cold air fluidization bed 15 may receive the second material to be dried after the hot air drying treatment from the hot air drying tank 14 to perform the cold air drying treatment on the second material to be dried after the hot air drying treatment to obtain the xylitol crystal product B. More descriptions regarding the xylitol crystal product B may be found in FIG. 2 and related descriptions thereof.

In some embodiments, the preparation system 20 may further comprise a microprocessor and an image sensor.

The image sensor refers to a sensing device that utilizes a photosensitive device to obtain an image. In some embodiments, the image sensor may include one or more photosensitive devices such as a photocoupling component, a complementary metal oxide semiconductor, or the like. In some embodiments, the image sensor may be arranged near a view window of a crystallization kettle. The image sensor may be configured to obtain a solution image. The crystallization kettle may include the first crystallization kettle 7 or the second crystallization kettle 12. More descriptions regarding the solution image may be found in FIG. 2 and related descriptions thereof.

The microprocessor refers to a computing and control core of the preparation system 20, which is a final execution unit for information processing and program operation, such as a central processing unit (CPU), a graphics processor, a field programmable logic gate array, or the like.

In some embodiments, the microprocessor may be configured to: determine, based on the solution image obtained from the image sensor, a crystallization precipitation rate of the crystallization kettle within at least one time interval; determine, based on the crystallization precipitation rate within the at least one time interval, a current crystallization phase; determine, based on the current crystallization phase, a current crystallization precipitation rate, and a current temperature of the crystallization kettle, a target temperature regulation amount of the crystallization kettle. More descriptions regarding the crystallization precipitation rate, the current crystallization phase, the current temperature of the crystallization kettle, and the target temperature regulation amount be found in FIG. 3 and related descriptions thereof.

In some embodiments, the microprocessor may be further configured to: determine, based on the solution image acquired from the image sensor, the crystallization precipitation rate of the crystallization kettle within the at least one time interval using a crystallization rate determination model. The crystallization rate determination model may be a machine learning model. More descriptions regarding the crystallization rate determination model may be found in FIG. 4 and related descriptions thereof.

In some embodiments, the microprocessor may be further configured to: predict, based on a candidate regulation parameter, the current crystallization phase, the current crystallization precipitation rate, and the current temperature of the crystallization kettle, a crystallization precipitation rate increment corresponding to the candidate regulation parameter through a precipitation prediction model, the precipitation prediction model being a machine learning model; and determine, based on the crystallization precipitation rate increment, the target temperature regulation amount of the crystallization kettle. More descriptions regarding the candidate regulation parameter, the precipitation prediction model, and the crystallization precipitation rate increment may be found in FIG. 5 and related descriptions thereof.

It is noted that the above description of the preparation system for the high-quality xylitol crystals and modules thereof is provided only for descriptive convenience, and does not limit the present disclosure to the scope of the embodiments cited. It is understood that for a person skilled in the art, after understanding the principle of the system, it may be possible to arbitrarily combine the individual modules or form a sub-system to be connected to other modules without departing from the principle. In some embodiments, the microprocessor and the image sensor disclosed in FIG. 1 may be different modules in a system, or a single module realizing the functions of two or more modules as described above. For example, the individual modules may share a common storage module, and the individual modules may each have a respective storage module. Such variations are within the scope of protection of the present disclosure.

Figure 2:
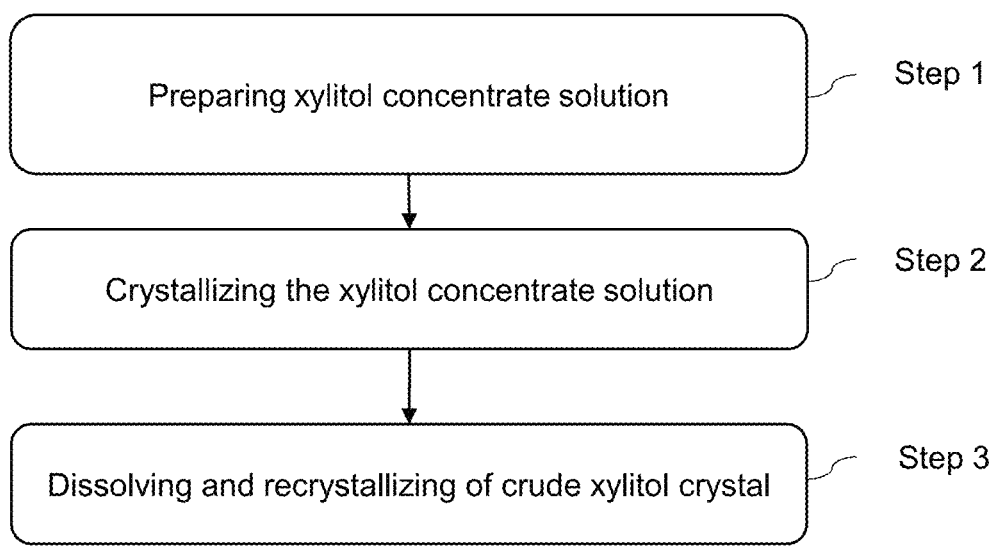
FIG. 2 is a flowchart illustrating an exemplary preparation method for high-quality xylitol crystals according to some embodiments of the present disclosure.

FIG. 2 is a main flowchart illustrating a preparation method for high-quality xylitol crystals according to some embodiments of the present disclosure. As illustrated in FIG. 2, a process 200 may include the following steps. In some embodiments, the process 200 may be performed by system 20 as described above.

Step 1, xylitol concentrate solution may be prepared.

In some embodiments, the system may blend and mix xylitol hydrogenation solution with primary centrifugal mother liquor delivered from a first centrifuge in a first proportion to obtain mixed material solution. A heat exchange treatment by a heat exchanger, a decolorization treatment by a decolorization tank, an ion exchange treatment by an ion exchange system, a filtration treatment by a microporous filter, and an evaporation treatment by a first evaporator may be performed on the mixed material solution, respectively, to obtain the xylitol concentrate solution. Merely by way of example, concentration of the xylitol concentrate solution may be within a range of 1200-1400 g/L, and purity of the xylitol concentrate solution may be within a range of 94-96%.

The xylitol concentrate solution refers to concentrated solution obtained by treating (e.g., the heat exchange treatment, the decolorization treatment, the ion exchange treatment, etc.) the mixed material solution of the xylitol hydrogenation solution and the primary centrifugal mother liquor. A centrifugal mother liquor refers to a liquid containing xylitol obtained by last centrifugal separation on centrifuge. For example, the primary centrifugal mother liquor may contain a xylitol sugar paste left over from the last centrifugation of the first centrifuge. In some embodiments, the first predetermined proportion may be determined based on manual experience or historical blending data of the mixed material solution. More descriptions regarding the xylitol sugar paste may be found in step 2 and related descriptions thereof.

In some embodiments, the system may perform the heat exchange treatment, the decolorization treatment, the ion exchange treatment, the filtration treatment, and the evaporation treatment on the mixed material solution by the heat exchanger, the decolorization tank, the ion exchange system, and the microporous filter, respectively, to obtain the xylitol concentrate solution. More descriptions regarding the heat exchanger, the decolorization tank, the ion exchange system, and the microporous filter may be found in FIG. 1 and related descriptions thereof.

In some embodiments, the system may perform the heat exchange treatment on the mixed material solution by the heat exchanger, such that temperature of the mixed material solution or the xylitol concentrate solution after the heat exchange treatment may satisfy a predetermined temperature condition. In some embodiments, the predetermined temperature condition may be set based on manual experience or demand temperatures for historical preparation of xylitol concentrate solutions, etc. In some embodiments, in step 1, the temperature of the xylitol concentrate solution may be within a range of 90-100° C. More descriptions regarding the heat exchanger and the heat exchange treatment may be found in FIG. 1 and related descriptions thereof.

In some embodiments of the present disclosure, by controlling the temperature of the xylitol concentrate solution, the concentration of the xylitol concentrate solution may be improved, so that the crude xylitol crystals with high purity can be obtained subsequently, thereby improving the quality of the prepared xylitol crystals.

Step 2, the xylitol concentrate solution may be crystallized.

In some embodiments, the system may cool and crystallize the xylitol concentrate solution in a first crystallization kettle for 8-12 h to obtain xylitol sugar paste, perform a separation treatment by a first centrifuge and a drying treatment by a fluidization drying bed on the xylitol sugar paste to obtain the crude xylitol crystals. The primary centrifugal mother liquor obtained by the separation treatment of the first centrifuge may backset to the blending tank through pipeline to be blended with the xylitol hydrogenation solution for reuse. Merely by way of example, purity of the crude xylitol crystals may be within a range of 98.5-99.8%, and pH<5.0, and purity of the primary centrifugal mother liquor may be within a range of 88-92%.

The xylitol sugar paste refers to mixture of saturated solution and crystal, the crystal is precipitated because the xylitol concentrate solution is supersaturated cause by decrease in solubility after cooling. In some embodiments, the xylitol sugar paste may include saturated solution and precipitated crystals. In some embodiments, the system may perform a cooling and crystallization treatment on the xylitol concentrate solution using the first crystallization kettle based on a predetermined crystallization time. The predetermined crystallization time may be determined based on manual experience or historical crystallization times of xylitol. Merely by way of example, the predetermined crystallization time may be within a range of 8-12 h. More descriptions regarding the first crystallization kettle may be found in the FIG. 1 and related descriptions thereof.

The crude xylitol crystals refer to first prepared xylitol crystals. The primary centrifugal mother liquor refers to residual solution obtained from the xylitol sugar paste after the separation treatment. The primary centrifugal mother liquor may contain part of the residual xylitol, which may be used for next preparation of the xylitol concentrate solution, such as the primary centrifugal mother liquor blended in step 1.

In some embodiments, the system may separate the xylitol sugar paste using the first centrifuge to obtain first material to be dried and the primary centrifugal mother liquor. The first material to be dried refers to crystals precipitated from the xylitol sugar paste. In some embodiments, the system may perform a drying treatment on the first material to be dried using a fluidization drying bed to obtain the crude xylitol crystals. More descriptions regarding the first centrifuge and the fluidization drying bed may be found in FIG. 1 and related descriptions thereof.

In some embodiments, in the step 2, the system may add xylitol crystal seeds during the cooling and crystallization treatment. Merely by way of example, an addition proportion of the xylitol crystal seeds may be within a range of 0.001-0.002% of solution mass, a mesh number of the xylitol crystal seeds may be within a range of 60-120 mesh, and a system temperature at same time of adding the xylitol crystal seeds may be within a range of 64-66° C.

Xylitol crystal seeds refer to additives that allow for the formation of crystal nuclei in a crystallization method to accelerate or facilitate growth of xylitol crystals. In some embodiments, a parameter of the xylitol crystal seeds may include one or more parameters, such as the addition proportion of the xylitol crystal seeds, the mesh number of the xylitol crystal seeds, the system temperature at same time of adding the xylitol crystal seeds, or the like. The system temperature at same time of adding the xylitol crystal seeds refers to solution temperature at the time of adding the xylitol crystal seeds, such as temperature of the xylitol concentrate solution. In some embodiments, the parameter of the xylitol crystal seeds may be set based on crystallization demand. For example, if the crystallization demand includes controlling the xylitol to crystallize more, the addition proportion of the xylitol crystal seeds, the mesh number of the xylitol crystal seeds, and the system temperature at same time of adding the xylitol crystal seeds may be increased.

In some embodiments of the present disclosure, by adding the xylitol crystal seeds, the rate of the cooling and crystallization treatment of the xylitol may be accelerated, and the xylitol sugar paste may be obtained in a more quickly and timely manner, thereby improving the efficiency of preparing the xylitol crystals.

Step 3, the crude xylitol crystals may be dissolved and recrystallized.

In some embodiments, the system may deliver the crude xylitol crystals to a xylitol dissolution tank to be dissolved by adding pure water, and then blend and mix dissolved crude xylitol crystals with secondary centrifugal mother liquor delivered from a second centrifuge in a second proportion to obtain dissolved xylitol mixture. The dissolved xylitol mixture may be concentrated by a second evaporator, crystallized by a second crystallization kettle, centrifuged by a second centrifuge, dried by hot air of hot air drying tank, and dried by cold air of a cold air fluidization bed in turn to obtain xylitol crystal product. The second centrifugal mother liquor obtained by the separation treatment of the second centrifuge may backset to the xylitol dissolution tank through pipeline to be mixed with crude xylitol crystal solution for reuse. Merely by way of example, purity of the xylitol crystal product may be greater than 99.8%, and pH>6.0.

The pure water refers to water in which electrolytes that are difficult to be removed from the water are removed to a certain extent, such as deep desalinated water, deionized water, or other liquids. The secondary centrifugal mother liquor refers to liquid containing xylitol crystals obtained after last centrifugal separation by the second centrifuge. Dissolved xylitol mixture is mixed solution of solution obtained by redissolving the crude xylitol crystals in the xylitol dissolution tank and the secondary centrifugal mother liquor. In some embodiments, the second predetermined proportion may be determined based on manual experience or historical blending data of the dissolved xylitol mixture. More descriptions regarding the xylitol dissolution tank may be found in FIG. 1 and related descriptions thereof.

In some embodiments, the system may sequentially perform a concentration treatment and a crystallization treatment on the dissolved xylitol mixture using the second evaporator and the second crystallization kettle to obtain the dissolved xylitol mixture after the crystallization treatment. In some embodiments, the system may separate the dissolved xylitol mixture after the crystallization treatment using the second centrifuge to obtain second material to be dried and the secondary centrifugal mother liquor.

The second material to be dried refers to crystals precipitated from the dissolved xylitol mixture after the crystallization treatment. In some embodiments, the system may sequentially perform a hot air drying treatment and a cold air drying treatment on the second material to be dried using the hot air drying tank and the cold air fluidization bed to obtain the xylitol crystal product. More descriptions regarding the second evaporator, the second crystallization kettle, the second centrifuge, the hot air drying tank, and the cold air fluidization bed may be found in FIG. 1 and related descriptions thereof.

In some embodiments of the present disclosure, the first prepared xylitol crystals may be dissolved by adding water in a certain ratio (e.g., the first predetermined proportion) to obtain xylitol solution with high purity. The xylitol solution may be recrystallized to prepare xylitol crystals with high pH and good flavor, which can improve the pH of the xylitol crystals and maintain the pH stable for a long time, and effectively improve the flavor of the xylitol crystals.

In some embodiments, in the step 3, the system may add the xylitol crystal seeds during the crystallization process in the second crystallization kettle. Merely by way of example, the addition proportion of the xylitol crystal seeds may be within a range of 0.001-0.002% of solution mass, the mesh number of the xylitol crystal seeds may be within a range of 60-120 mesh, and the system temperature at the time of adding the xylitol crystal seeds may be within a range of 64-66° C. More descriptions regarding the xylitol crystal seeds may be found in the step 2 and related descriptions thereof.

In some embodiments of the present disclosure, by adding the xylitol crystal seeds, the rate of the crystallization treatment in the second crystallization kettle may be accelerated, and the recrystallized xylitol solution (i.e., the dissolved xylitol mixture after the crystallization treatment) may be obtained in a more quickly and timely manner, thereby improving the efficiency of preparing the xylitol crystals.

Figure 3:
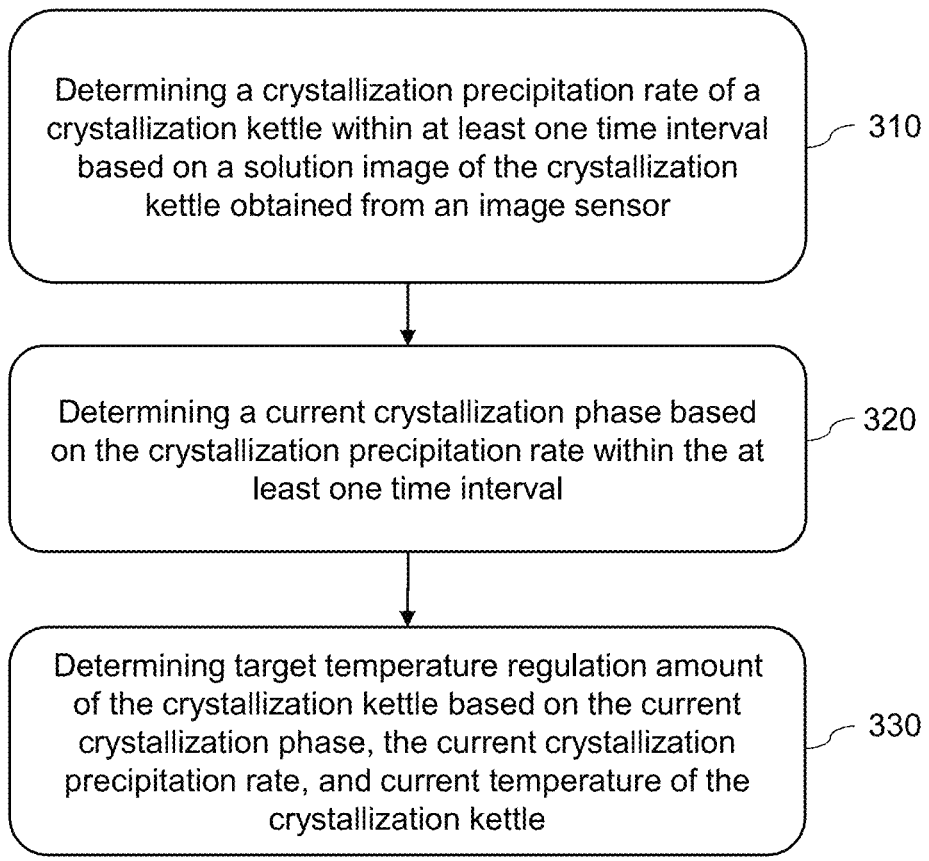
FIG. 3 is a schematic diagram illustrating a process for determining a target temperature regulation amount of a crystallization kettle according to some embodiments of the present disclosure.

FIG. 3 is a schematic diagram illustrating a process for determining a target temperature regulation amount of a crystallization kettle according to some embodiments of the present disclosure. As illustrated in FIG. 3, a process 300 may include the following steps. In some embodiments, the process 300 may be performed by a microprocessor described above.

Step 310, a crystallization precipitation rate of a crystallization kettle within at least one time interval may be determined based on a solution image of the crystallization kettle obtained from an image sensor.

The crystallization kettle may include a first crystallization kettle or a second crystallization kettle. For example, the microprocessor may determine that a regulation object is the first crystallization kettle or the second crystallization kettle, and obtain information related to the corresponding crystallization kettle such as the solution image, or the like, so as to subsequently regulate the corresponding crystallization kettle.

The solution image refers an image of solution contained in the crystallization kettle, such as an image of xylitol concentrate solution subjected to a cooling and crystallization process in the first crystallization kettle or an image of dissolved xylitol mixture subjected to the crystallization process in the second crystallization kettle. In some embodiments, the solution image of the crystallization kettle may reflect a crystallization state of the solution in the crystallization kettle, such as a crystallization distribution, a count of crystallization particles, or the like.

In some embodiments, the microprocessor may periodically obtain the solution image of the crystallization kettle based on a predetermined period duration using the image sensor. The predetermined period duration may be set based on manual experience, a crystallization regulation demand, etc. For example, if the crystallization regulation demand includes making crystallization regulation in time, a relatively short predetermined period duration may be set.

In some embodiments, the microprocessor may also be triggered to obtain the solution image based on other means such as a predetermined obtaining condition using the image sensor. The predetermined obtaining condition may include a fluctuation in the crystallization precipitation rate at various time points relative to a standard precipitation rate curve. For example, the crystallization rate in the crystallization kettle may be continuously determined. If an actual crystallization precipitation rate deviates from the standard precipitation rate curve from a certain time point, the crystallization precipitation rate may fluctuate, which satisfies the predetermined obtaining condition, then the microprocessor may be triggered to obtain the image of the xylitol concentrate solution. More descriptions regarding the image sensor may be found in FIG. 1 and related descriptions thereof.

The crystallization precipitation rate refers to a count of crystallization particles precipitated from solution per unit time period. In some embodiments, a change in the count of crystallization particles may be correlated to a change in pixels of the solution image. For example, the more changes in the pixel of the solution image for two consecutive frames, the more crystallization particles precipitated from the solution during a time interval corresponding to the two adjacent frames. Assuming that obtaining time points corresponding to the solution image of the two consecutive frames are 1 s and 2 s, the time interval corresponding to the two adjacent frames may be [1 s, 2 s].

In some embodiments, the microprocessor may determine the crystallization precipitation rate of the crystallization kettle within the at least one time interval based on the solution image of the crystallization kettle within the at least one time interval through various ways such as a table, a vector library, etc. For example, the microprocessor may calculate a pixel difference between the solution images of the two consecutive frames, query a pixel difference range corresponding to the pixel difference using a table of predetermined rate correspondences based on the pixel difference, and determine a reference crystallization precipitation rate corresponding to the pixel difference range as the crystallization precipitation rate within the time interval corresponding to the two consecutive frames.

The table of predetermined rate correspondences may be established based on a pixel difference between historical solution images of the two consecutive frames and historical crystallization precipitation rates corresponding to the historical solution images of the two consecutive frames. Both the historical solution images and the historical crystallization precipitation rates may be obtained by the microprocessor through a network or by manual input, etc.

In some embodiments, the table of predetermined rate correspondences may also be established through a plurality of experiments. For example, if pixel differences of a plurality of sets of solution images of the two consecutive frames are obtained at a same crystallization precipitation rate through the plurality of experiments, the microprocessor may count a mean pixel difference range of the plurality sets of the solution images to obtain a pixel difference range corresponding to the crystallization precipitation rate.

It should be noted that when the microprocessor obtains a first frame of image, the microprocessor may calculate the first frame of image with reference to a standard solution image to determine a crystallization precipitation rate in a corresponding first time interval. The standard solution image may be obtained by the microprocessor through the web or based on an initial image of historical solution, etc. More descriptions regarding the crystalline precipitation rate may be found in FIG. 4 and related descriptions thereof.

Step 320, a current crystallization phase may be determined based on the crystallization precipitation rate within the at least one time interval.

The current crystallization phase refers to a phase in which crystals precipitate out from a liquid or gas phase at a current time point. In some embodiments, the crystallization phase may include: a saturation phase, a nucleation phase, a growth phase, or the like. In the saturation phase, transient microscopic crystallization particles may appear in the solution, and the crystallization precipitation rate corresponding to the saturation phase may be slow. In the nucleation phase, crystal nuclei may simultaneously appear in plasmas within the solution, or appear in local cells, and the crystallization precipitation rate corresponding to the nucleation phase may be fast. In the growth phase, crystals may grow on the crystal nuclei within the solution, and crystallization precipitation rate corresponding to the growth phase may be moderate.

In some embodiments, the microprocessor may determine, based on the crystallization precipitation rate of the crystallization kettle within the at least one time interval, the current crystallization phase through various ways such as a predetermined table, a vector library, or the like. For example, the microprocessor may search, based on the crystallization precipitation rate within the at least one time interval, look up a reference crystallization precipitation rate in a table of crystallization phase correspondences that is similar to the crystallization precipitation rate, and determine a crystallization phase corresponding to the reference crystallization precipitation rate as the current crystallization phase.

The table of crystallization phase correspondences may be established based on crystallization precipitation rates of at least one historical time interval and crystallization phases corresponding to the crystallization precipitation rates. The crystallization precipitation rates of the historical time intervals and the crystallization phases corresponding to the crystallization precipitation rates may be obtained by the microprocessor via a network or manual input, or the like. For example, the table of crystallization phase correspondences may be constructed based on historical crystallization precipitation rate curves throughout the entire crystallization process in historical data.

Step 330, target temperature regulation amount of the crystallization kettle may be determined based on the current crystallization phase, the current crystallization precipitation rate, and current temperature of the crystallization kettle.

The current crystallization precipitation rate refers to a crystallization precipitation rate within a current time interval. More descriptions regarding the current crystallization phase and the crystallization precipitation rate may be found in steps 310-320 and related descriptions thereof.

The temperature of the crystallization kettle refers to temperature of solution in the crystallization kettle, such as temperature of xylitol concentrate solution in a first crystallization kettle. In some embodiments, the temperature of the crystallization kettle temperature may affect a solution saturation point, affecting a crystal precipitation rate. For example, as the temperature of the crystallization kettle decreases, the solution saturation point of the solution also decreases, which causes solution that is originally in an unsaturated state to become saturated, thus accelerating the crystal precipitation rate. In some embodiments, the microprocessor may collect the current temperature of the crystallization kettle using sensing components such as a temperature sensor, a thermometer, or the like. The current temperature of the crystallization kettle refers to temperature of the crystallization kettle at the current time point.

The target temperature regulation amount refers to amount of temperature to be regulated. In some embodiments, a sign of the target temperature regulation amount may be correlated to a direction of temperature regulation. If the sign of the target temperature regulation amount is negative, the microprocessor may regulate the temperature of the crystallization kettle to reduce an absolute value of the target temperature regulation amount.

In some embodiments, the microprocessor may determine, based on the current crystallization phase, the current crystallization precipitation rate, and the current temperature of the crystallization kettle, the target temperature regulation amount of the crystallization kettle in various ways such as table lookup, vector library matching, or the like.

Merely by way of example, the microprocessor may construct, based on the current crystallization phase, the current crystallization precipitation rate, and the current temperature of the crystallization kettle, a vector to be matched, retrieve in a temperature vector database of a reference matching vector similar to the vector to be matched, and determine a reference temperature regulation amount corresponding to the reference matching vector as the target temperature regulation amount.

A plurality of reference matching vectors and a plurality of reference temperature regulation amounts corresponding to the plurality of reference matching vectors may be stored in the temperature vector database. In some embodiments, the microprocessor may perform, based on historical crystallization phases, historical crystallization precipitation rates, historical temperatures of the crystallization kettle, and historical temperature regulation amounts of the crystallization kettle in historical databases, clustering, and determine crystallization phases, crystallization precipitation rates, and temperatures of the crystallization kettle corresponding to clustering centers formed by clustering as the reference matching vectors. The reference temperature regulation amounts may be constructed based on the historical temperature regulation amounts of the crystallization kettle corresponding to the reference matching vectors, or may be determined by manual labeling. More descriptions regarding the target temperature regulation amount may be found in FIG. 5 and related descriptions thereof.

In some embodiments of the present disclosure, the crystallization precipitation rate may be determined by the solution image of the crystallization kettle, and the current crystallization phase may be determined based on the crystallization precipitation rate, and the target temperature regulation amount of the crystallization kettle may be accurately determined with reference to the current temperature of the crystallization kettle, so that the solution saturation point of the solution can be accurately changed to regulate the crystal precipitation rate, thereby improving the preparation efficiency of the xylitol crystals.

Figure 4:
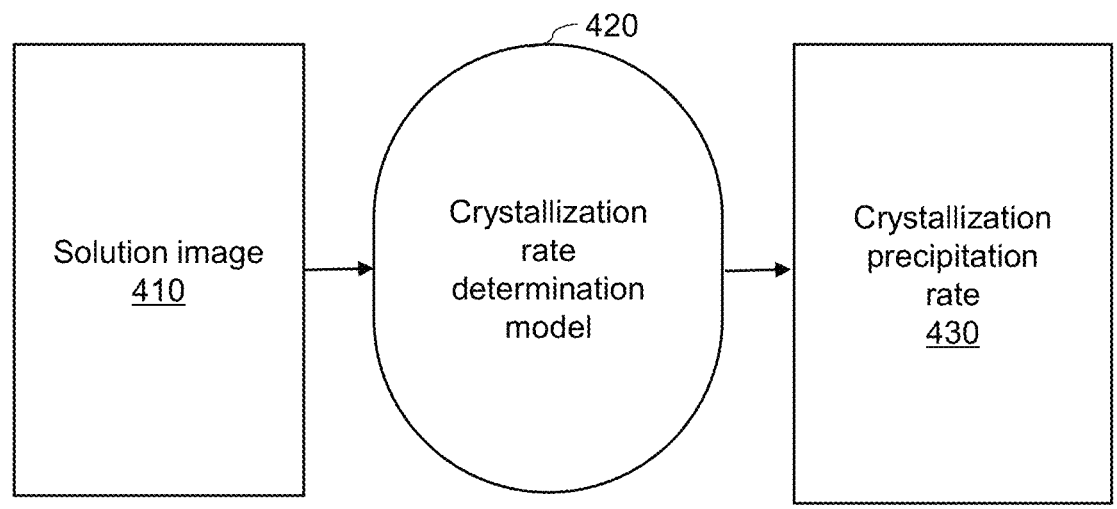
FIG. 4 is a schematic diagram illustrating a process for determining a crystallization precipitation rate according to some embodiments of the present disclosure.

FIG. 4 is a schematic diagram illustrating a process for determining a crystallization precipitation rate according to some embodiments of the present disclosure. In some embodiments, as illustrated in FIG. 4, a microprocessor may also determine, based on a solution image 410 obtained from an image sensor, a crystallization precipitation rate 430 of a crystallization kettle within at least one time interval using a crystallization rate determination model 420. The crystallization rate determination model 420 may be a machine learning model.

In some embodiments, the crystallization rate determination model 420 may be a machine learning model, such as a recurrent neural network (RNN), etc.

In some embodiments, an input of the crystallization rate determination model 420 may include the solution image 410 obtained by the image sensor. In some embodiments, an output of the crystallization rate determination model 420 may include the crystallization precipitation rate 430 of the crystallization kettle within the at least one time interval. More descriptions regarding the solution image 410 and the crystallization precipitation rate 430 may be found in FIGS. 2-3 and related descriptions thereof.

In some embodiments, the crystallization rate determination model 420 may be obtained based on training of a large amount of training data. The training data may include training samples and labels. For example, the training samples may include sample solution images, and the labels of the training samples may include sample crystallization precipitation rates of the crystallization kettle within the at least one time interval.

The training samples may include solution images of the crystallization kettle within a historical time period in a historical database, and the labels of the training samples may include crystallization precipitation rates of the crystallization kettle in the corresponding historical time period. In some embodiments, the microprocessor may obtain the historical database for preparing xylitol crystals through various means, such as a network, manual input, or the like.

In some embodiments of the present disclosure, an operation may be performed using the crystallization rate determination model based on the solution image, so that the crystallization precipitation rate within the at least one time interval can be quickly determined, and a target temperature regulation amount of the crystallization kettle can be determined in time, thereby improve the preparation efficiency of the xylitol crystals.

Figure 5:
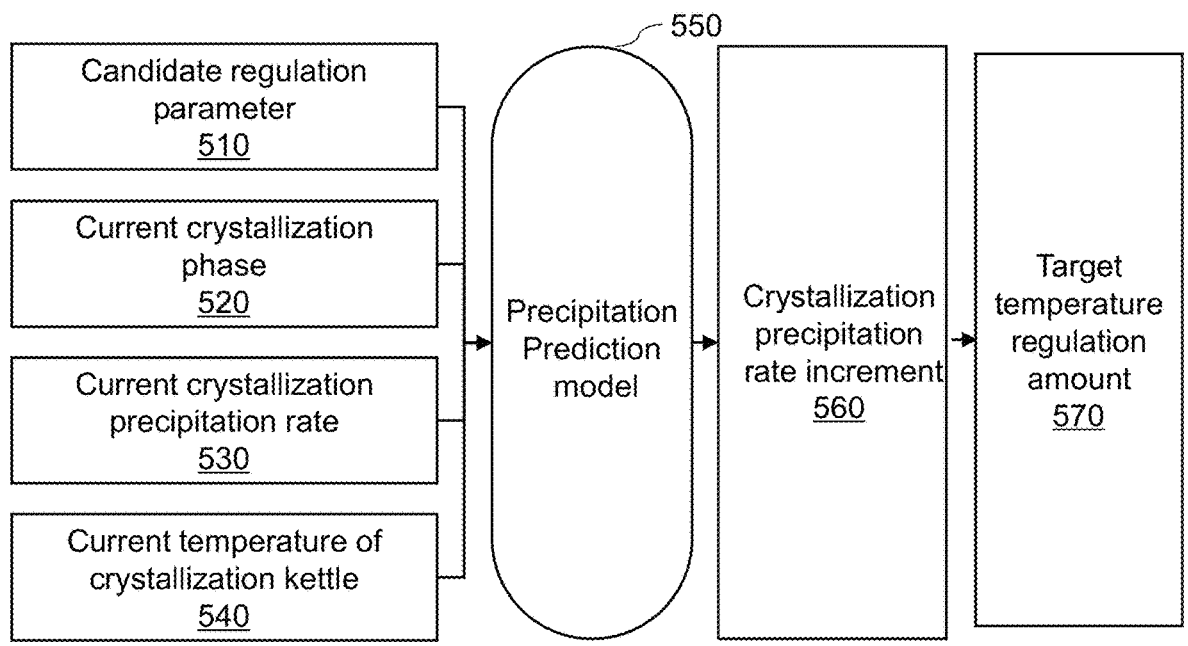
FIG. 5 is a schematic diagram illustrating a process for determining a target temperature regulation amount according to some embodiments of the present disclosure.

FIG. 5 is a schematic diagram illustrating a process for determining target temperature regulation amount according to some embodiments of the present disclosure. In some embodiments, as illustrated in FIG. 5, a microprocessor may also determine, based on a candidate regulation parameter 510, a current crystallization phase 520, a current crystallization precipitation rate 530, and current temperature of a crystallization kettle 540, a crystallization precipitation rate increment 560 corresponding to the candidate regulation parameter 510 through a precipitation prediction model 550; and determine, based on the crystallization precipitation rate increment 560, target temperature regulation amount 570 of the crystallization kettle.

In some embodiments, the precipitation prediction model 550 may be a machine learning model, such as a recurrent neural network (RNN), etc.

In some embodiments, an input of the precipitation prediction model 550 may include the candidate regulation parameter 510, the current crystallization phase 520, the current crystallization precipitation rate 530, and the current temperature of the crystallization kettle 540.

The candidate regulation parameter 510 refers to predetermined temperature regulation amount of the crystallization kettle. In some embodiments, the microprocessor may randomly generate at least one candidate regulation parameter 510, or may select the at least one candidate regulation parameter 510 based on historical temperature regulation amounts in a historical database. More descriptions regarding the current crystallization phase 520, the current crystallization precipitation rate 530, and the current crystallization kettle temperature 540 may be found in FIGS. 3-4 and related descriptions thereof.

In some embodiments, an output of the precipitation prediction model 550 may include the crystallization precipitation rate increment 560 corresponding to the candidate regulation parameter 510.

The crystallization precipitation rate increment 560 refers to a value of change in crystallization precipitation rate after temperature regulation is performed using the candidate regulation parameter 510. In some embodiments, the crystallization precipitation rate increment 560 may be a difference between a crystallization precipitation rate within a future time interval and the current crystallization precipitation rate 530. The crystallization precipitation rate within the future time interval may be the crystallization precipitation rate of the crystallization kettle within the future time interval after the temperature regulation is performed using the candidate regulation parameter 510.

In some embodiments, the precipitation prediction model 550 may be obtained based on training of a large amount of training data. The training data may include training samples and labels. For example, the training samples may include sample candidate regulation parameters, sample crystallization phases, sample crystallization precipitation rates, and sample temperature of the crystallization kettle. The labels of the training samples may include a sample crystallization precipitation rate increment.

The training samples may include historical regulation parameters, historical crystallization phases, historical crystallization precipitation rates, and historical temperatures of the crystallization kettle within a first historical time period in the historical database, and the labels of the training samples may include historical crystallization precipitation rate increments within a second historical time period. The second historical time period may be later than the first historical time period. The historical crystallization precipitation rate increments within the second historical time period may be determined based on a difference between the historical crystallization precipitation rates within the second historical time period and the historical crystallization precipitation rates within the first historical time period.

In some embodiments, the predicted crystallization precipitation rate increment 560 may reflect regulation effect of the candidate regulation parameter 510. For example, if a sign of the crystallization precipitation rate increment 560 is positive, it may be indicated that the crystallization precipitation rate within the future time interval is greater than the current crystallization precipitation rate 530, which may reflect that the regulation effect of the candidate regulation parameter 510 is relatively good. In addition, the larger a value of the crystallization precipitation rate increment 560, the better the regulation effect of the candidate regulation parameter 510.

In some embodiments, the microprocessor may also determine, based on the crystallization precipitation rate increment 560, the target temperature regulation amount 570 of the crystallization kettle in various ways, such as sorting, querying a table, or the like. For example, the microprocessor may determine the crystallization precipitation rate increment 560 with the positive sign by sorting, and select a candidate regulation parameter corresponding to a largest value of the crystallization precipitation rate increment 560 as the target temperature regulation amount 570 of the crystallization kettle.

In some embodiments of the present disclosure, by generating a plurality of candidate regulation parameters in advance and predicting crystallization precipitation rate increments corresponding to the plurality of candidate regulation parameters, an appropriate parameter can be quickly selected from the plurality of candidate regulation parameters as the target temperature regulation amount, thereby improving the preparation efficiency of xylitol crystals. In addition, the prediction efficiency can be accelerated by utilizing the machine learning model for prediction, thereby improving the timeliness of temperature regulation.

The preparation system and the preparation method for the high-quality xylitol crystals of the present disclosure are further described below by way of specific Examples.

Example 1

The first Example of a preparation method for high-quality xylitol crystals of the present disclosure comprises the following steps.

Step 11, xylitol hydrogenation solution A was blended with primary centrifugal mother liquor C in a first predetermined proportion. Blending solution was sequentially refined and concentrated by heat exchanger 2, decolorization tank 3, ion exchange system 4, microporous filter 5, and first evaporator 6 to obtain xylitol concentrate solution with temperature of 100° C., concentration of 1200 g/L, and purity of 94%. More descriptions regarding the first predetermined proportion may be found in FIG. 2 and related descriptions thereof.

Step 12, constant vacuum degree of the first crystallization kettle 7 was maintained at −0.095 MPa to further evaporate the xylitol concentrate solution. When temperature of the first crystallization kettle 7 dropped to 65° C., 0.001% xylitol crystal seeds (80-100 mesh) were added, and the system was maintained at constant temperature of 65° C. for evaporation and crystallization for 8 h. Finally, a crude xylitol crystal with purity of 99.5% and pH of 4.87 was obtained by centrifugal separation treatment of the first centrifuge 8 and fluidization drying treatment of the fluidization drying bed 9. At the same time, the primary centrifugal mother liquor C with purity of 90% obtained by the centrifugal separation treatment of the first centrifuge 8 was backset to the blending tank 1.

Step 13, pure water was added to the crude xylitol crystal with purity of 99.5% to be dissolved for blending with secondary centrifugal mother liquor D to obtain secondary blending solution with xylitol purity of 98.2%. The secondary blending solution was further concentrated by second evaporator 11 to concentration of 1350 g/L, then enter to second crystallization kettle 12. The second crystallization kettle 12 was maintained at constant vacuum degree of −0.095 MPa and constant temperature of 65° C., and 0.001% xylitol crystal seeds (80-100 mesh) were added for evaporation and crystallization for 8 h. Finally, the xylitol crystal B with purity of 99.97% was obtained by centrifugal separation treatment of the second centrifuge 13, hot air drying treatment of the second hot air drying tank 14, and cold air drying treatment of the cold air fluidization bed 15. At the same time, the secondary centrifugal mother liquor D obtained by the centrifugal separation treatment of the second centrifuge 13 was backset to the xylitol dissolution tank 10.

The acidity of prepared xylitol crystal B was measured according to the method in the Chinese Pharmacopoeia. Xylitol solution was prepared with pure water in a proportion of 10 g crystal to 20 ml water. The pH of the xylitol solution in this Example was measured to be 6.06. After the obtained xylitol crystal B were stored at room temperature for one week, the pH of the xylitol solution was measured to be 6.03 using the same method. After the xylitol crystal was stored at room temperature for one month, the pH of the xylitol solution was measured to be 6.01 using the same method.

Figure 6:
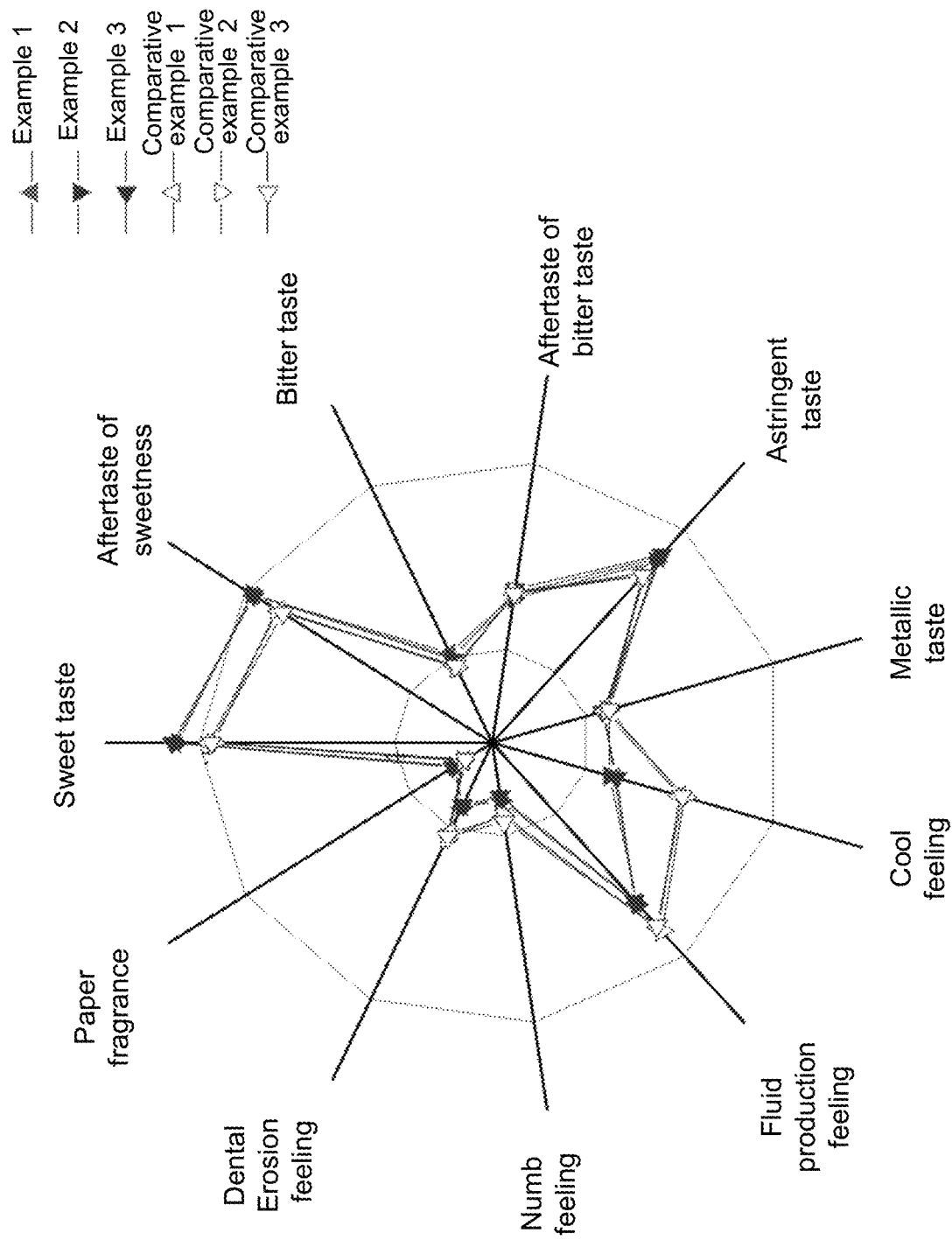
FIG. 6 is a schematic diagram illustrating flavor evaluation of xylitol crystals prepared in various Examples of the present disclosure and Comparative Examples.

The flavor evaluation test was performed on the xylitol crystal prepared in Example 1, and results were obtained as shown in FIG. 6.

Example 2

The second Example of a preparation method for high-quality xylitol crystals of the present disclosure comprises the following steps.

Step 21, xylitol hydrogenation solution A was blended with primary centrifugal mother liquor C in a first predetermined proportion. Blending solution was sequentially refined and concentrated by heat exchanger 2, decolorization tank 3, ion exchange system 4, microporous filter 5, and first evaporator 6 to obtain xylitol concentrate solution with temperature of 90° C., concentration of 1400 g/L, and purity of 94%. More descriptions regarding the first predetermined proportion may be found in FIG. 2 and related descriptions thereof.

Step 22, constant vacuum degree of the first crystallization kettle 7 was maintained at −0.095 MPa to further evaporate the xylitol concentrate solution. When temperature of the first crystallization kettle 7 dropped to 64° C., 0.001% xylitol crystal seeds (100-120 mesh) were added, and the system was maintained at constant temperature of 64° C. for evaporation and crystallization for 12 h. Finally, crude xylitol crystal with purity of 99.6% and pH of 4.9 was obtained by centrifugal separation treatment of the first centrifuge 8 and fluidization drying treatment of the fluidization drying bed 9. At the same time, the primary centrifugal mother liquor C with purity of 89.5% obtained by the centrifugal separation treatment of the first centrifuge 8 was backset to the blending tank 1.

Step 23, pure water was added to the crude xylitol crystal with purity of 99.6% to be dissolved for blending with secondary centrifugal mother liquor D to obtain secondary blending solution with xylitol purity of 98.4%. The secondary blending solution was further concentrated by second evaporator 11 to concentration of 1380 g/L, then enter to the second crystallization kettle 12. The second crystallization kettle 12 was maintained at constant vacuum degree of −0.095 MPa and constant temperature of 65° C., and 0.001% xylitol crystal seeds (100-120 mesh) were added for evaporation and crystallization for 10 h. Finally, the xylitol crystal B with purity of 99.97% was obtained by centrifugal separation treatment of the second centrifuge 13, hot air drying treatment of the second hot air drying tank 14, and cold air drying treatment of the cold air fluidization bed 15. At the same time, the secondary centrifugal mother liquor D obtained by the centrifugal separation treatment of the second centrifuge 13 was backset to the xylitol dissolution tank 10.

The acidity of prepared xylitol crystal B was measured according to the method in the Chinese Pharmacopoeia. Xylitol solution was prepared with pure water in a proportion of 10 g crystal to 20 ml water. The pH of the xylitol solution in this Example was measured to be 6.12. After the obtained xylitol crystal B was stored at room temperature for one week, the pH of the xylitol solution was measured to be 6.08 using the same method. After the xylitol crystal was stored at room temperature for one month, the pH of the xylitol solution was measured to be 6.05 using the same method.

The flavor evaluation test was performed on the xylitol crystal prepared in Example 2, and results were obtained as shown in FIG. 6.

Example 3

The third Example of a preparation method for high-quality xylitol crystals of the present disclosure comprises the following steps.

Step 31, xylitol hydrogenation solution A was blended with primary centrifugal mother liquor C in a first predetermined proportion to obtain blending solution with xylitol purity of 96%. The blending solution was sequentially refined and concentrated by heat exchanger 2, decolorization tank 3, ion exchange system 4, microporous filter 5, and first evaporator 6 to obtain xylitol concentrate solution with temperature of 95° C. and concentration of 1350 g/L. More descriptions regarding the first predetermined proportion may be found in FIG. 2 and related descriptions thereof.

Step 32, constant vacuum degree of the first crystallization kettle 7 was maintained at −0.095 MPa to further evaporate the xylitol concentrate solution. When temperature of the first crystallization kettle 7 dropped to 66° C., 0.002% xylitol crystal seeds (60-80 mesh) were added, and the system was maintained at constant temperature of 66° C. for evaporation and crystallization for 10 h. Finally, the crude xylitol crystal with purity of 99.7% and pH of 4.99 was obtained by centrifugal separation treatment of the first centrifuge 8 and fluidization drying treatment of the fluidization drying bed 9. At the same time, the primary centrifugal mother liquor C with purity of 92% obtained by the centrifugal separation treatment of the first centrifuge 8 was backset to the blending tank 1.

Step 33, pure water was added to the crude xylitol crystal with purity of 99.7% to be dissolved for blending with secondary centrifugal mother liquor D to obtain secondary blending solution with xylitol purity of 98.4%. The secondary blending solution was further concentrated by second evaporator 11 to concentration of 1400 g/L, then enter to the second crystallization kettle 12. The second crystallization kettle 12 was maintained at constant vacuum degree of −0.095 MPa and constant temperature of 65° C., and 0.002% xylitol crystal seeds (60-80 mesh) were added for evaporation and crystallization for 10 h. Finally, the xylitol crystal B with purity of 100% was obtained by centrifugal separation treatment of the second centrifuge 13, hot air drying treatment of the second hot air drying tank 14, and cold air drying treatment of the cold air fluidization bed 15. At the same time, the secondary centrifugal mother liquor D obtained by the centrifugal separation treatment of the second centrifuge 13 was backset to the xylitol dissolution tank 10.

The acidity of prepared xylitol crystal B was measured according to the method in the Chinese Pharmacopoeia. Xylitol solution was prepared with pure water in a proportion of 10 g crystal to 20 ml water. The pH of the xylitol solution in this Example was measured to be 6.09. After the obtained xylitol crystal B was stored at room temperature for one week, the pH of the xylitol solution was measured to be 6.07 using the same method. After the xylitol crystals were stored at room temperature for one month, the pH of the xylitol solution was measured to be 6.05 using the same method.

The flavor evaluation test was performed on the xylitol crystal prepared in Example 3, and results were obtained as shown in FIG. 6.

The following comparative experiments were conducted to further illustrate the improvement effects of the present disclosure.

Comparative Example 1

The first comparative examples of a preparation method for xylitol crystals of the present disclosure comprises the following steps.

Step D11, xylitol hydrogenation solution A was blended with primary centrifugal mother liquor C in a first predetermined proportion to obtain blending solution with xylitol purity of 94%. The blending solution was sequentially refined and concentrated by heat exchanger 2, decolorization tank 3, ion exchange system 4, microporous filter 5, and first evaporator 6 to obtain xylitol concentrate solution with temperature of 95° C. and concentration of 1300 g/L. More descriptions regarding the first predetermined proportion may be found in FIG. 2 and related descriptions thereof.

Step D12, constant vacuum degree of the first crystallization kettle 7 was maintained at −0.095 MPa to further evaporate the xylitol concentrate solution. When temperature of the first crystallization kettle 7 dropped to 64° C., 0.001% xylitol crystal seeds (80-100 mesh) were added, and the system was maintained at constant temperature of 64° C. for evaporation and crystallization for 10 h. Finally, the xylitol crystal with purity of 99.8% was obtained by centrifugal separation treatment of the first centrifuge 8 and fluidization drying treatment of the fluidization drying bed 9. At the same time, the primary centrifugal mother liquor C with purity of 90% obtained by the centrifugal separation treatment of the first centrifuge 8 was backset to the blending tank 1.

The acidity of prepared xylitol crystal was measured according to the method in the Chinese Pharmacopoeia. Xylitol solution was prepared with pure water in a proportion of 10 g crystal to 20 ml water. The pH of the xylitol solution in this comparative example was measured to be 5.02. After the obtained xylitol crystals was stored at room temperature for one week, the pH of the xylitol solution was measured to be 4.85 using the same method. After the xylitol crystal was stored at room temperature for one month, the pH of the xylitol solution was measured to be 4.64 using the same method.

The flavor evaluation test was performed on the xylitol crystal prepared in comparative example 1, and results were obtained as shown in FIG. 6.

Comparative Example 2

The second comparative example of a preparation method for xylitol crystals of the present disclosure comprises the following steps.

Step D21, xylitol hydrogenation solution A was blended with primary centrifugal mother liquor C in a first predetermined proportion to obtain blending solution with xylitol purity of 94.5%. The blending solution was sequentially refined and concentrated by heat exchanger 2, decolorization tank 3, ion exchange system 4, microporous filter 5, and first evaporator 6 to obtain xylitol concentrate solution with temperature of 100° C. and concentration of 1200 g/L. More descriptions regarding the first predetermined proportion may be found in FIG. 2 and related descriptions thereof.

Step D22, constant vacuum degree of the first crystallization kettle 7 was maintained at −0.095 MPa to further evaporate the xylitol concentrate solution. When temperature of the first crystallization kettle 7 dropped to 65° C., 0.002% xylitol crystal seeds (100-120 mesh) were added, and the system was maintained at constant temperature of 65° C. for evaporation and crystallization for 8 h. Finally, the xylitol crystal with purity of 99.75% was obtained by centrifugal separation treatment of the first centrifuge 8 and fluidization drying treatment of the fluidization drying bed 9. At the same time, the primary centrifugal mother liquor C with purity of 91% obtained by the centrifugal separation treatment of the first centrifuge 8 was backset to the blending tank 1.

The acidity of prepared xylitol crystal was measured according to the method in the Chinese Pharmacopoeia. Xylitol solution was prepared with pure water in a proportion of 10 g crystal to 20 ml water. The pH of the xylitol solution in this Contrast was measured to be 5.04. After the obtained xylitol crystal was stored at room temperature for one week, the pH of the xylitol solution was measured to be 4.81 using the same method. After the xylitol crystal was stored at room temperature for one month, the pH of the xylitol solution was measured to be 4.68 using the same method.

The flavor evaluation test was performed on the xylitol crystal prepared in comparative example 2, and results were obtained as shown in FIG. 6.

Comparative Example 3

The third comparative example of a preparation method for xylitol crystals of the present disclosure comprises the following steps.

Step D31, xylitol hydrogenation solution A was blended with primary centrifugal mother liquor C in a first predetermined proportion to obtain blending solution with xylitol purity of 96%. The blending solution was sequentially refined and concentrated by heat exchanger 2, decolorization tank 3, ion exchange system 4, microporous filter 5, the first evaporator 6 to obtain xylitol concentrate solution with temperature of 92° C. and concentration of 1400 g/L. More descriptions regarding the first predetermined proportion may be found in FIG. 2 and related descriptions thereof.

Step D32, constant vacuum degree of the first crystallization kettle 7 was maintained at −0.095 MPa to further evaporate the xylitol concentrate solution. When temperature of the first crystallization kettle 7 dropped to 66° C., 0.001% xylitol crystal seeds (100-120 mesh) were added, and the system was maintained at constant temperature of 66° C. for evaporation and crystallization for 12 h. Finally, the xylitol crystal with purity of 99.7% was obtained by centrifugal separation treatment of the first centrifuge 8 and fluidization drying treatment of the fluidization drying bed 9. At the same time, the primary centrifugal mother liquor C with purity of 92% obtained by the centrifugal separation treatment of the first centrifuge 8 was backset to the blending tank 1.

The acidity of prepared xylitol crystal was measured according to the method in the Chinese Pharmacopoeia. Xylitol solution was prepared with pure water in a proportion of 10 g crystal to 20 ml water. The pH of the xylitol solution in this comparative example was measured to be 5.03. After the obtained xylitol crystal was stored at room temperature for one week, the pH of the xylitol solution was measured to be 4.90 using the same method. After the xylitol crystal was stored at room temperature for one month, the pH of the xylitol solution was measured to be 4.73 using the same method.

The flavor evaluation test was performed on the xylitol crystal prepared in comparative example 3, and results were obtained as shown in FIG. 6.

The results of pH and flavor evaluation of the xylitol crystals prepared in the above Examples and comparative examples are summarized as shown in Table 3 and FIG. 6. It can be seen from Table 3 that the pH of the xylitol crystals of Examples 1-3 are above 6.0, and the pH of the xylitol crystals decrease no more than 0.1 after one month of storage; while the pH of the xylitol crystals of comparative examples 1-3 are only about 5.0, and the pH of the xylitol crystals decrease more than 0.3 after one month of storage. These data indicate that the pH of the xylitol crystals can be significantly increased and stabilized by recrystallization. In addition, it can be seen from the flavor evaluation radar chart in FIG. 6 that sweet taste, aftertaste of sweetness and other attributes of the xylitol crystal products prepared in Examples 1-3 that are preferred by consumers are enhanced compared to those of comparative examples, and unfavorable attributes such as dental erosion, numbness, or the like are weakened compared to those of comparative examples, which further indicates that the xylitol crystals prepared by the method described in the present disclosure have significantly improved flavor.

TABLE 3

A correspondence table between the implementation sample of xylitol solution and measured pH

| Implementation sample of xylitol solution | pH of xylitol | pH of xylitol after one week storage | pH of xylitol after one month storage |
|---|---|---|---|
| Example 1 | 6.06 | 6.03 | 6.01 |
| Example 2 | 6.12 | 6.08 | 6.05 |

TABLE 3-continued

A correspondence table between the implementation sample of xylitol solution and measured pH

| Implementation sample of xylitol solution | pH of xylitol | pH of xylitol after one week storage | pH of xylitol after one month storage |
|---|---|---|---|
| Example 3 | 6.09 | 6.07 | 6.05 |
| Comparative example 1 | 5.02 | 4.85 | 4.64 |
| Comparative example 2 | 5.04 | 4.81 | 4.68 |
| Comparative example 3 | 5.03 | 4.90 | 4.73 |

One or more embodiments of the present disclosure further provide a monitoring device for a battery status of an energy storage station. The monitoring device may comprise at least one processor and at least one storage. The at least one storage may be configured to store computer instructions. The at least one processor may be configured to execute at least a part of the computer instructions to implement the preparation method for high-quality xylitol crystals as described in any of the above embodiments.

The processor refers to a computing and control core of the monitoring device for a battery status of an energy storage station, which is a final execution unit for information processing and program operation, such as a central processing unit (CPU), a graphics processor, a field programmable logic gate array, or the like. In some embodiments, the processor may perform the preparation method for the high-quality xylitol crystals as illustrated in FIGS. 2-5. More descriptions regarding the preparation method may be found in the related descriptions above.

One or more embodiments of the present disclosure further provide a non-transitory computer-readable storage medium comprising computer instructions that, when read by a computer, may direct the computer to implement the preparation method for the high-quality xylitol crystals as described in any of the above embodiments.

The basic concept has been described above. Obviously, for those skilled in the art, the above detailed disclosure is only an example, and does not constitute a limitation to the present disclosure. Although not expressly stated here, those skilled in the art may make various modifications, improvements and corrections to the present disclosure. Such modifications, improvements and corrections are suggested in this disclosure, so such modifications, improvements and corrections still belong to the spirit and scope of the exemplary embodiments of the present disclosure.

Meanwhile, the present disclosure uses specific words to describe the embodiments of the present disclosure. For example, "one embodiment", "an embodiment", and/or "some embodiments" refer to a certain feature, structure or characteristic related to at least one embodiment of the present disclosure. Therefore, it should be emphasized and noted that references to "one embodiment" or "an embodiment" or "an alternative embodiment" two or more times in different places in the present disclosure do not necessarily refer to the same embodiment. In addition, certain features, structures, or characteristics in one or more embodiments of the present disclosure may be properly combined.

In addition, unless clearly stated in the claims, the sequence of processing elements and sequences described in the present disclosure, the use of counts and letters, or the use of other names are not used to limit the sequence of processes and methods in the present disclosure. While the foregoing disclosure has discussed by way of various examples some embodiments of the invention that are presently believed to be useful, it should be understood that such detail is for illustrative purposes only and that the appended claims are not limited to the disclosed embodiments, but rather, the claims are intended to cover all modifications and equivalent combinations that fall within the spirit and scope of the embodiments of the present disclosure. For example, although the implementation of various components described above may be embodied in a hardware device, it may also be implemented as a software only solution, e.g., an installation on an existing server or mobile device.

In the same way, it should be noted that in order to simplify the expression disclosed in this disclosure and help the understanding of one or more embodiments of the invention, in the foregoing description of the embodiments of the present disclosure, sometimes multiple features are combined into one embodiment, drawings or descriptions thereof. This method of disclosure does not, however, imply that the subject matter of the disclosure requires more features than are recited in the claims. Rather, claimed subject matter may lie in less than all features of a single foregoing disclosed embodiment.

In some embodiments, counts describing the quantity of components and attributes are used. It should be understood that such counts used in the description of the embodiments use the modifiers "about", "approximately" or "substantially" in some examples. Unless otherwise stated, "about", "approximately" or "substantially" indicates that the stated figure allows for a variation of ±20%. Accordingly, in some embodiments, the numerical parameters used in the disclosure and claims are approximations that can vary depending upon the desired characteristics of individual embodiments. In some embodiments, numerical parameters should consider the specified significant digits and adopt the general digit retention method. Although the numerical ranges and parameters used in some embodiments of the present disclosure to confirm the breadth of the range are approximations, in specific embodiments, such numerical values are set as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A preparation system for high-quality xylitol crystal, comprising a blending tank, a heat exchanger, a decolorization tank, an ion exchange system, a microporous filter, a first evaporator, a first crystallization kettle, a first centrifuge, a fluidization drying bed, a xylitol dissolution tank, a second evaporator, a second crystallization kettle, a second centrifuge, a hot air drying tank, and a cold air fluidization bed which are sequentially connected through pipelines; wherein the first centrifuge and the second centrifuge are provided with liquid outlet, respectively, the liquid outlet of the first centrifuge is connected with first inlet of the blending tank through pipeline, the liquid outlet of the second centrifuge is connected with first inlet of the xylitol dissolution tank through pipeline, the blending tank is provided with second inlet for receiving material to be treated, the xylitol dissolution tank is provided with a water inlet for pure water, the cold air fluidization bed is provided with a product outlet, the material to be treated is xylitol hydrogenation solution, and material output from the product outlet of the cold air fluidization bed is xylitol crystal product.

2. The preparation system of claim 1, wherein the preparation system further comprises a microprocessor and an image sensor, the image sensor is arranged near a view window of a crystallization kettle and configured to obtain a solution image; the crystallization kettle includes the first crystallization kettle or the second crystallization kettle; and the microprocessor is configured to:
determine, based on the solution image obtained from the image sensor, a crystallization precipitation rate of the crystallization kettle within at least one time interval;
determine, based on the crystallization precipitation rate within the at least one time interval, a current crystallization phase; and
determine, based on the current crystallization phase, a current crystallization precipitation rate, and a current temperature of the crystallization kettle, a target temperature regulation amount of the crystallization kettle.

3. The preparation system of claim 2, wherein the microprocessor is further configured to:
determine, based on the solution image obtained from the image sensor, the crystallization precipitation rate of the crystallization kettle within the at least one time interval through a crystallization rate determination model, the crystallization rate determination model being a machine learning model.

4. The preparation system of claim 2, wherein the microprocessor is further configured to:
predict, based on a candidate regulation parameter, the current crystallization phase, the current crystallization precipitation rate, and the current temperature of the crystallization kettle, a crystallization precipitation rate increment corresponding to the candidate regulation parameter through a precipitation prediction model, the precipitation prediction model being a machine learning model; and
determine, based on the crystallization precipitation rate increment, the target temperature regulation amount of the crystallization kettle.

5. A preparation method for high-quality xylitol crystal, comprising:
step 1, preparing xylitol concentrate solution, including blending and mixing xylitol hydrogenation solution with primary centrifugal mother liquor delivered from first centrifuge in a first proportion to obtain mixed material solution, and then performing a heat exchange treatment by heat exchanger, a decolorization treatment by decolorization tank, an ion exchange treatment by ion exchange system, a filtration treatment by microporous filter, and an evaporation treatment by first evaporator on the mixed material solution, respectively, to obtain the xylitol concentrate solution; wherein a concentration of the xylitol concentrate solution is within a range of 1200-1400 g/L, and a purity of the xylitol concentrate solution is within a range of 94-96%;
step 2, crystallizing the xylitol concentrate solution, including cooling and crystallizing the xylitol concentrate solution in first crystallization kettle for 8-12 h to obtain xylitol sugar paste, performing a separation treatment by the first centrifuge and a drying treatment by a fluidization drying bed on the xylitol sugar paste to obtain crude xylitol crystal, and the primary centrifugal mother liquor obtained by the separation treatment of the first centrifuge back-setting to the blending tank through pipeline to be blended with the xylitol hydrogenation solution for reuse; wherein the purity of the crude xylitol crystal is within a range of 98.5-99.8%, and pH<5.0, and the purity of the primary centrifugal mother liquor is within a range of 88-92%; and
step 3, dissolving and recrystallizing the crude xylitol crystal, including delivering the crude xylitol crystal to xylitol dissolution tank to be dissolved by adding pure water, and then blending and mixing dissolved crude xylitol crystal with secondary centrifugal mother liquor delivered from a second centrifuge in a second proportion to obtain dissolved xylitol mixture, the dissolved xylitol mixture being concentrated by second evaporator, crystallized by second crystallization kettle, centrifuged by the second centrifuge, dried by hot air of hot air drying tank, and dried by cold air of a cold air fluidization bed in turn to obtain xylitol crystal product, and the second centrifugal mother liquor obtained by the separation treatment of the second centrifuge back-setting to the xylitol dissolution tank through pipeline to be mixed with crude xylitol crystal solution for reuse; wherein the purity of the xylitol crystal product is greater than 99.8%, and pH>6.0.

6. The preparation method of claim 5, wherein in step 1, temperature of the xylitol concentrate solution is within a range of 90-100° C.

7. The preparation method of claim 5, wherein in step 2, xylitol crystal seeds are added during cooling and crystallization process; wherein
an addition proportion of the xylitol crystal seeds is within a range of 0.001-0.002% of solution mass, a mesh number of the xylitol crystal seeds is within a range of 60-120 mesh, and system temperature at same time of adding the xylitol crystal seeds is within a range of 64-66° C.

8. The preparation method of claim 5, wherein in step 3, xylitol crystal seeds are added during the crystallization process in the second crystallization kettle; wherein
an addition proportion of the xylitol crystal seeds is within a range of 0.001-0.002% of solution mass, a mesh number of the xylitol crystal seeds is within a range of 60-120 mesh, and system temperature at same time of adding the xylitol crystal seeds is within a range of 64-66° C.

9. The preparation method of claim 5, wherein the preparation method further comprises:

determining, based on a solution image of a crystallization kettle obtained from an image sensor, a crystallization precipitation rate of the crystallization kettle within at least one time interval;

determining, based on the crystallization precipitation rate within the at least one time interval, a current crystallization phase; and determining, based on the current crystallization phase, a current crystallization precipitation rate, and a current temperature of the crystallization kettle, a target temperature regulation amount of the crystallization kettle;

wherein the crystallization kettle is a first crystallization kettle or a second crystallization kettle.

10. The preparation method of claim 9, wherein the determining, based on a solution image of the crystallization kettle obtained from an image sensor, a crystallization precipitation rate of the crystallization kettle within at least one time interval includes:

determining, based on the solution image obtained from the image sensor, the crystallization precipitation rate of the crystallization kettle within the at least one time interval through a crystallization rate determination model, the crystallization rate determination model being a machine learning model.

11. The preparation method of claim 9, wherein the determining a target temperature regulation amount includes:

predicting, based on a candidate regulation parameter, the current crystallization phase, the current crystallization precipitation rate, and the current temperature of the crystallization kettle, a crystallization precipitation rate increment corresponding to the candidate regulation parameter through a precipitation prediction model, the precipitation prediction model being a machine learning model; and determining, based on the crystallization precipitation rate increment, the target temperature regulation amount of the crystallization kettle.

* * * * *